United States Patent [19]

Vilasi

[11] Patent Number: 4,722,335
[45] Date of Patent: Feb. 2, 1988

[54] EXPANDABLE ENDOTRACHEAL TUBE

[76] Inventor: Joseph A. Vilasi, 37 Wagon Wheel La., Dix Hills, N.Y. 11746

[21] Appl. No.: 920,752

[22] Filed: Oct. 20, 1986

[51] Int. Cl.$^4$ ............................................. A61M 16/00
[52] U.S. Cl. ............................. 128/207.14; 128/207.15
[58] Field of Search ..................... 128/207.14, 207.15, 128/200.26, 343; 604/104

[56] References Cited

U.S. PATENT DOCUMENTS 4,054,135 10/1977 Berman .......................... 128/200.26
4,211,234 7/1980 Fisher ............................ 128/200.26
4,601,713 7/1986 Fugua .................................. 128/343

Primary Examiner—Edward M. Coven
Assistant Examiner—J. P. Lacyk
Attorney, Agent, or Firm—Leonard Belkin

[57] ABSTRACT

An expandable endotracheal tube and the like comprising a pair of overlapping extended segments. A piston drive mechanism actuated by air under pressure is disposed between the segments to effect the expansion of the tube in situ. Slidable dovetail joints insure that the segments slide only circumferentially with respect to each other. In another embodiment, the two segments are fused along one overlapping edge and a pair of catheters extend circumferentially with one entering the other.

20 Claims, 6 Drawing Figures

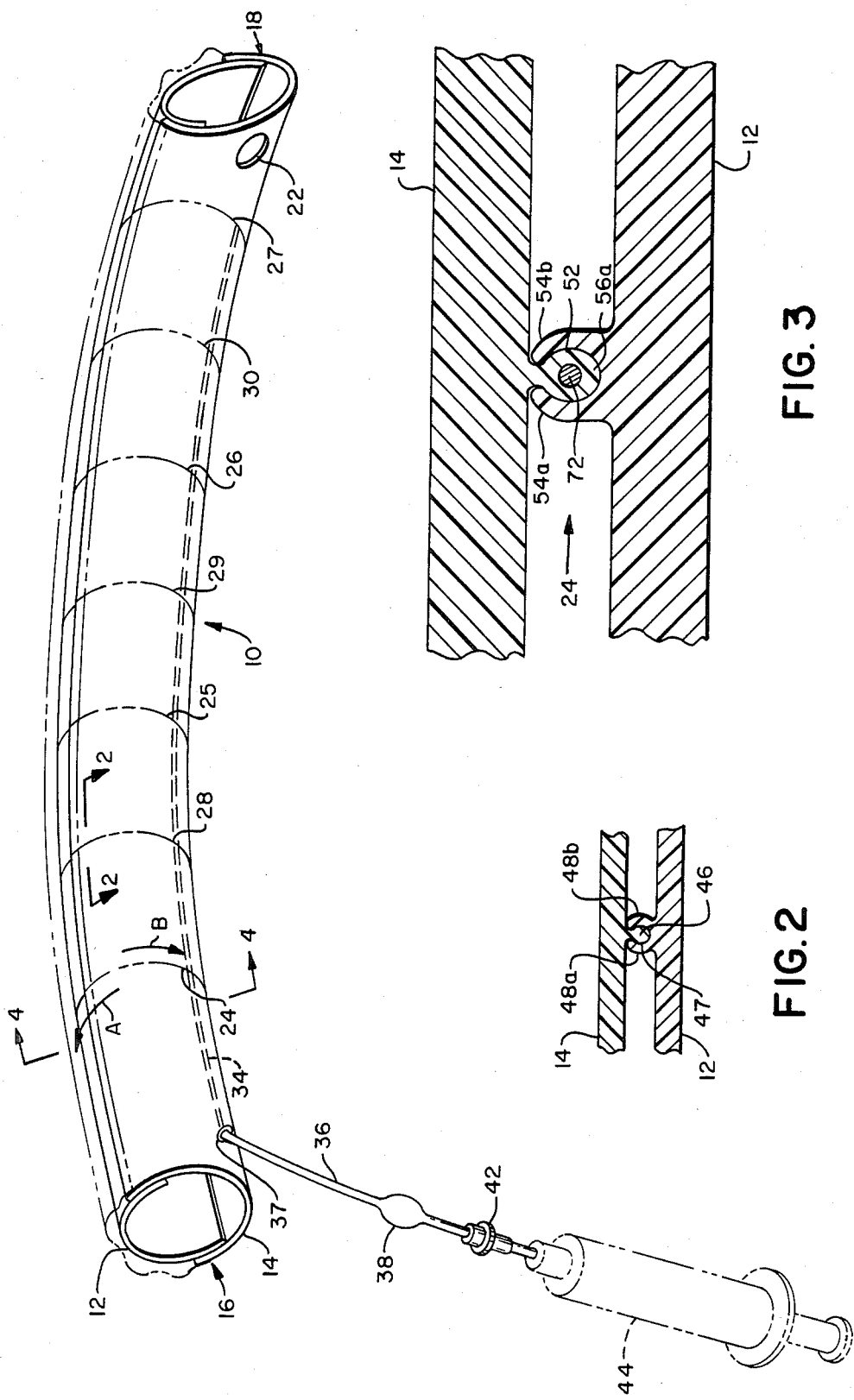

EXPANDABLE ENDOTRACHEAL TUBE

BACKGROUND OF THE INVENTION

This invention relates to expandable endotracheal tubes and more generally to devices adapted to be inserted into a body opening for carrying out therapeutic and other medical procedures.

An endotracheal tube typically is employed for insertion in a patient through his mouth for the purpose of ventilating his lungs. The tube passes through the normally restricted glottis or passageway between the vocal chords and may terminate adjacent the entrance to the bronchial tubes. To insure proper delivery to the lungs of the gases employed in the ventilation procedure, a off mounted on the far or distal end of the tube is inflated in situ to prevent back flow around the tube.

To accommodate patients having differently sized trachea, there is generally available to the medical practitioner a variety of endotracheal tubes of different diameters to permit selection of the proper size tube for the patient. In order to provide the most unobstructed passageway to the lungs it is desirable to insert the largest possible diameter tracheal tube acceptable to the patient.

Factors which limit the size of tube which can be utilized for a particular patient include the glottic passageway and the presence of the cuff on the outside of the distal end of the tube. Another factor is that the endotracheal tubes come in discrete sizes. To avoid possible damage to the vocal chords, it is quite often in the interest of the safety of the patient necessary to insert a smaller sized tube than the patient could safely tolerate because the next larger size is unacceptable.

In the case of children the vocal chord openings are much narrower than in adults so that there is a further restriction on the size of the diameter which can be employed, and in some children it is not possible or feasible to employ the cuff to prevent the backflow.

In addition, in some situations, the endotracheal tube must be inserted through the nose which limits further the diameter which can be tolerated.

In my U.S. Pat. No. 3,968,800 there is disclosed an adjustable endotracheal tube which was designed to overcome the problems and drawbacks associated with existing endotracheal tubes. The patented arrangement is complex and lacks the flexibility necessary to accommodate sufficiently well the varying shapes of trachea found in different patients. Another drawback is that the diameter of the tube is increased uniformly along its length and thus is limited to the expansion of the glottis in most cases. As a result there may be some backflow present.

SUMMARY IF THE INVENTION

This invention overcomes or reduces many of the problems associated with endotracheal tubes and the like now in use and expandable tubes which have been proposed for use.

In the present invention it is possible to insert the endotracheal tube and then to expand it to approximate exactly the glottic size of the patient until any back flow ceases. In addition, an important feature of this invention is the simple and economic construction combined with a high degree of reliability. With this arrangement, backflow is completely eliminated without the need for the use of an inflatable cuff.

One preferred embodiment of this invention is a device for insertion into a body opening comprising an extended tube-like member made up of a pair of first and second transversely curved segments, one of which overlaps the other to form said tube-like member. The two segments are joined by a plurality of spaced slidable dovetail joints each disposed along a circumference of the pair between the overlapping portions of the segments so that slidable movement of the segments with respect to each other causes changes in the circumference of the member at that location. Adjacent the proximal end of the device is located actuator means to pressurize a gas which upon being activated causes the segments to slide with respect to each other at specific locations along the length of the tube to expand the circumference of the member at those locations and retain the segments in their expanded state. In this arrangement expansion of the circumference is limited only by the space within the patient. Depending upon the flexibility of the material used for the segments, expansion may be different at each location thereby permitting the tube-like member to conform closely to the body opening into which it is inserted. Removal of the device is facilitated by depressurizing the actuator means which permits relaxation and retraction of the segments at the joints to facilitate withdrawal of the tube-like member from the body opening.

Other embodiments of this invention involve other configurations in which the same principles are incorporated.

It is thus a principal object of this invention to provide an endotracheal tube of simple and reliable construction which can be expanded in situ.

Other objects and advantages of this invention will hereinafter become obvious from the following description of preferred embodiments of this invention.

BRIEF DESCRIPTION OF THE FIGURES

FIG. 1 is an isometric view of an endotracheal tube embodying the principles of this invention.

FIG. 2 is a section view along 2—2 of FIG. 1.

FIG. 3 is a section view along 3—3 of FIG. 4.

DETAILED DESCRIPTION OF THE PREFERRED EMBODIMENT

Figure 4:
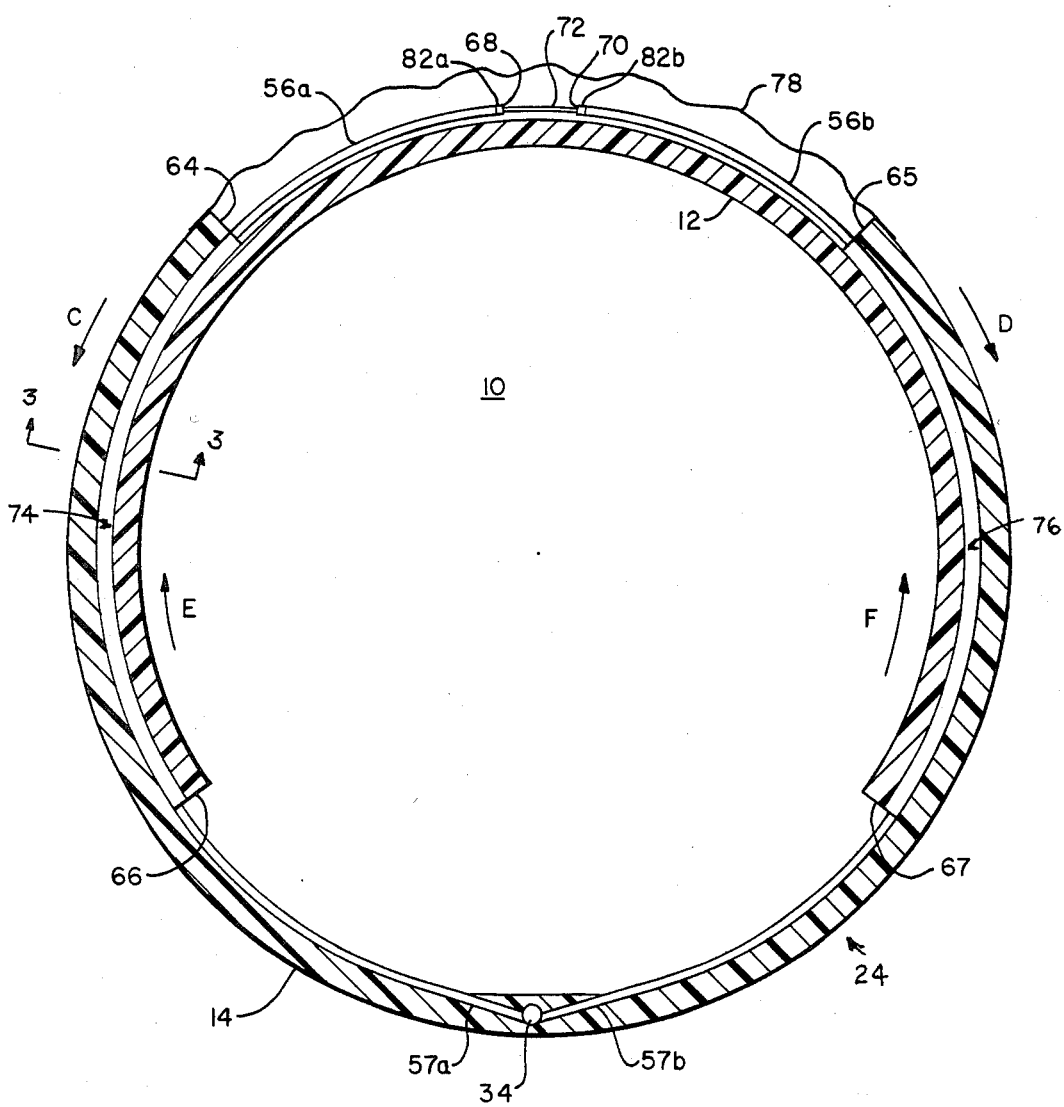
FIG. 4 is a section view along 4—4 of FIG. 1.

In the following description of the preferred embodiments, it is understood that while the devices described are endotracheal tubes the invention is equally applicable to other devices for insertion into body openings such as bronchoscopes, vascular and cervical dilators, and the like. In addition, while reference is made to tubes or tube-like members, it is understood that the cross section may be circular, oval, or any other configuration suitable for the particular application to which the principles of this invention are applicable.

Referring to FIG. 1, there is shown an endotracheal tube 10 which embodies the principles of this invention. Tube 10 consists of a pair of extended, transversely curved segments 12 and 14 with the latter overlapping the former in the manner illustrated. The overall configuration of tube 10 is similar to that of the conventional endotracheal tube having a generally arced shape with a proximal end 16 and a distal end 18, the latter cut at a bias and having an opening 22 for facilitating the discharge of the gas being employed for ventilating the lungs of the patient. When tube 10 is inserted into the patient through the oral or nasal cavity, distal end 18 would terminate in the trachea adjacent the entrance to the bronchial tubes, while proximal end 16 would extend out from the mouth or nose of the patient. Not shown are the conventional adaptors which would plug in or otherwise be attached to proximal end 16 for supplying the ventilating gases.

Segments 12 and 14 are preferably made from an elastomeric material such as rubber, soft plastic and the like enabling it to be inserted and conform to the shape of the body opening into which tube 10 is being inserted. Depending on the thickness of the walls making up tube 10, the degree of flexibility of the device can be selected for purposes to be described below.

Indicated in schematic fashion in FIG. 1 are the locations of four spaced and identical slidable expansion joints 24, 25, 26, 27; identical slidable dovetail joints 28, 29, and 30; and a supply line 34 in the wall of outer segment 14 for supplying air under pressure to the joints 24–27 to effect the expansion of tube 10 in the manner to be described below. Slidable dovetail joints 28, 29, and 30 are not actuated but insure proper relative movement and orientation of segments 12 and 14.

Air under pressure is delivered to supply line 34 by a tube 36 and opening 37 in the wall of segment 14. A conventional arrangement may be employed for this purpose consisting of tube 36, inflatable bellows 38, an adaptor 42 containing a one-way flap valve (not shown) to prevent back flow once the system is pressurized, and a syringe 44 shown in phantom to pressurize the system.

In FIG. 1, tube 10 is shown in its protracted state, prior to insertion into the patient.

Details of slidable dovetail joint 28 are shown in FIG. 2. Outer segment 14 is provided with an extended male-like member or protuberance 46 which slides in an extended female-like member or socket 47 formed by a pair of side walls 48a and 48b mounted on the outer surface of inner segment 12. The shapes of socket 47 and protuberance 46 are such as to resist separation once the latter is snapped into the former. Thus, protuberance 46 may be bulb shaped as illustrated and socket 47 have an opening on the bottom greater than the opening at the top of the two wide walls 48a and 48b. It is understood that the degree of retention of the connection of the parts at the joint can be determined at the time of manufacture by the size of the protuberance as well as the degree of flexibility of the material. In any event, when segments 12 and 14 are joined as seen in FIG. 2, they are readily slidable with respect to each other as indicated by arrows A and B in FIG. 1. As indicated earlier, all of the joints 28, 29, and 30 are identical.

For details of expansion joints 24, 25, 26, and 27, reference is made in FIG. 3, where details of joint 24 are illustrated. In the expansion joint, inner segment 12 is provided with the female-like member or socket 52 formed by a pair of side walls 54a and 54b. Within socket 52 extends a hollow catheter or tube 56a which is fused as illustrated to the inside wall of segment 14.

For details of the interconnection between supply line 34 and joint 24 (as well as identical joints 25, 26, and 27) so as to effect the slidable movement of segments 12 and 14 with respect to each other in order to expand the circumference of tube 10 at joint 24, reference is made to FIG. 4.

As seen in FIG. 4, supply line 34 comprises an opening which passes through the wall of segment 14. At joint 24, a pair of catheters 56a and 56b slope outwardly from communication with supply line 34 through openings 57a and 57b flaring outwardly from supply line 34. Catheters 56a and 56b are fused to and run along the inner surface of segment 14. Catheters 56a and 56b fit between side walls 54a and 54b of inner segment 12 as previously noted. Segment 14 terminates at edges 64 and 65 and segment 12 terminates at edges 66 and 67. Catheters 56a and 56b extend past edges 64 and 65 of segment 14 and cover almost the complete circumference of tube 10 and terminate at edges 68 and 70, respectively.

It should be noted that expansion joints 24–27 and slidable dovetail joints 28–30 are shown as being at right angles to supply line 34. As long as all the joints are parallel to each other they may be at some other suitable angle to supply line 34. Hence, when reference is made to movement along a circumference of said tube, this would include movement along the direction of said joints even if other than at right angles to said supply line which generally runs parallel to the axis of said tube.

A flexible, metallic wire or stilet 72 of arcuate shape bridges the space between edges 68 and 70 of catheters 56a and 56b entering the latter at both edges 68 and 70 and terminating in locations 74 and 76. When supply line 34 is pressurized resulting in catheters 56a and 56b becoming pressurized, the latter function as a cylinder and stilet 72 functions like a piston so that the two sides of segment 14 move in the direction of arrows C and D, while the two sides of segment 12 move in the direction of arrows E and F, as the spaces within catheters 56a and 56b expand circumferentially to accommodate the pressurized gas within as the result of the gas acting against the exposed edges of stilet 72 at locations 74 and 76.

A membrane 78 of thin plastic film initially wrinkled as illustrated joins edges 64 and 65 of segment 14 to perform three functions. First, it is a backup to contain any pressurized gas leaking out of catheters 56a and 56b past stilet 72, and second, it protects the patient against the exposed edges of outer segment 14 during insertion. Thirdly, it limits the expansion of tube 10. To prevent gas from leaking out of catheters 56a and 56b at ends 68 and 70 where stilet 72 enters, a rubber membranous injection site of conventional design is incorporated into ends 68 and 70 of catheters 56a and 56b. These sites are indicated by numeral 82a and 82b. FIG. 4 illustrates tube 10 prior to expansion. When expansion occurs, membrane 78 becomes taut.

In the operation of endotracheal tube 10, the latter is first inserted into the trachea of the patient in usual fashion, ordinarily through the mouth. After tube 10 is properly located, syringe 44 is plugged into adaptor 42 and the system is pressurized by pumping syringe 44. Pressurization is indicated when bladder 38 becomes inflated. Syringe 44 is then removed and a check valve (not shown) within adaptor 42 retains pressurization.

During pressurization, at each expansion joint 24, 25, 26, and 27, segments 12 and 14 will slide apart as described in connection with FIG. 4. At each location, tube 12 will expand to fill the available space at that point in the trachea of the patient depending on the wall thickness and flexibility of member 10. In the glottic passageway, tube 10 will widen the opening through the vocal chords. By increasing wall thickness and thereby reducing flexibility, expansion of member 10 can be made less variable along its length. Without the presence of an inflatable cuff as employed in present arrangements, there will be the largest possible passageway into the lungs and little or no backflow due to the close fitting which is obtained. Slidable dovetail joints 28, 29, and 30 prevent any movement of segments 12 and 14 with respect to each other in an axial direction.

When it is necessary to withdraw tube 10, the check valve within adaptor 42 is released by inserting a syringe into the opening in adaptor 42 to open the valve. Membrane 78 which is elastic in construction will help to collapse tube 10 sufficiently to permit its easy withdrawal, although the slidable dovetail joints are sufficiently free as to permit contraction of segments 12 and 14 during withdrawl of tube 10.

Figure 5:
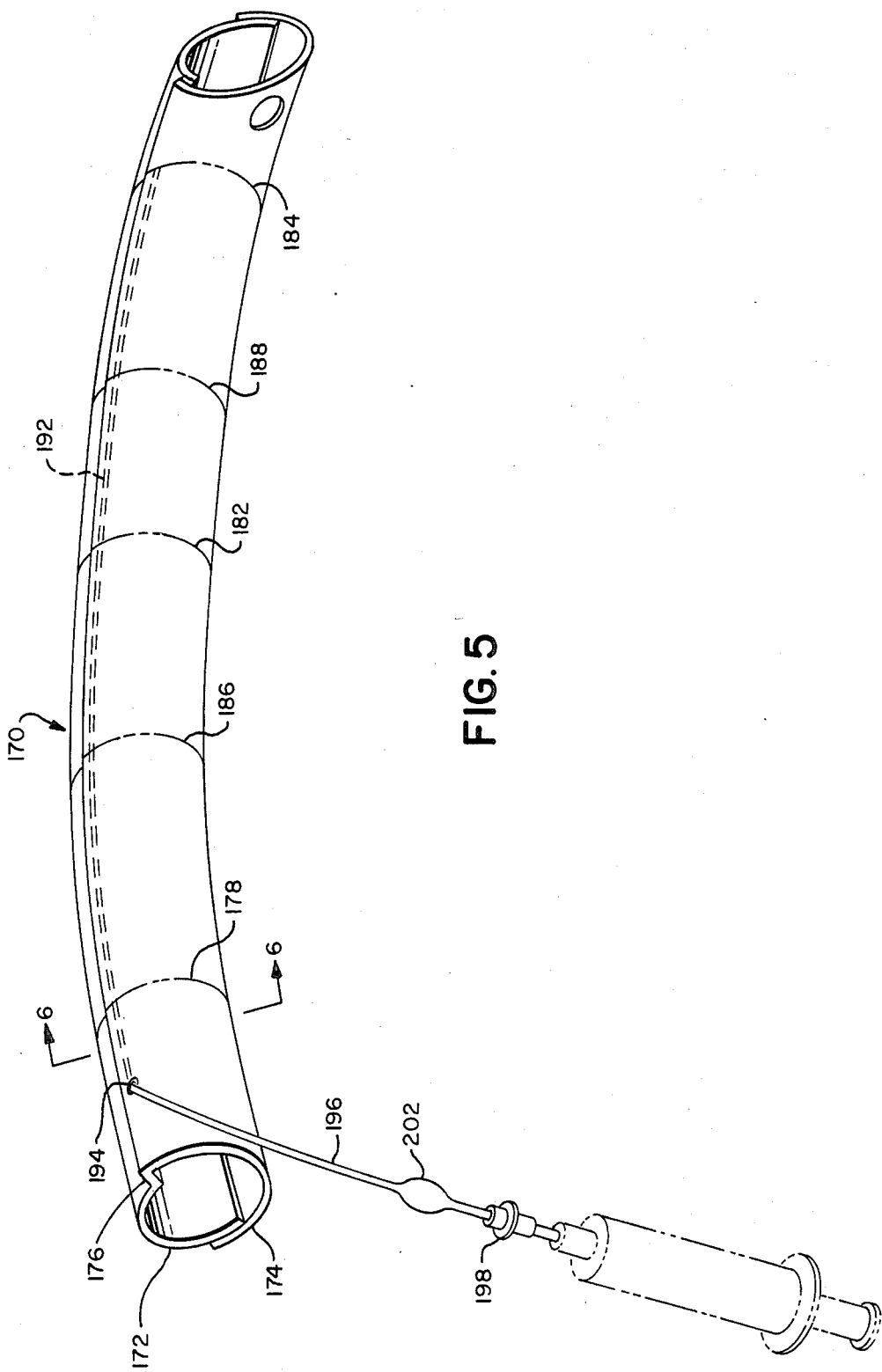
FIG. 5 is an isometric view of another embodiment of this invention.
Figure 6:
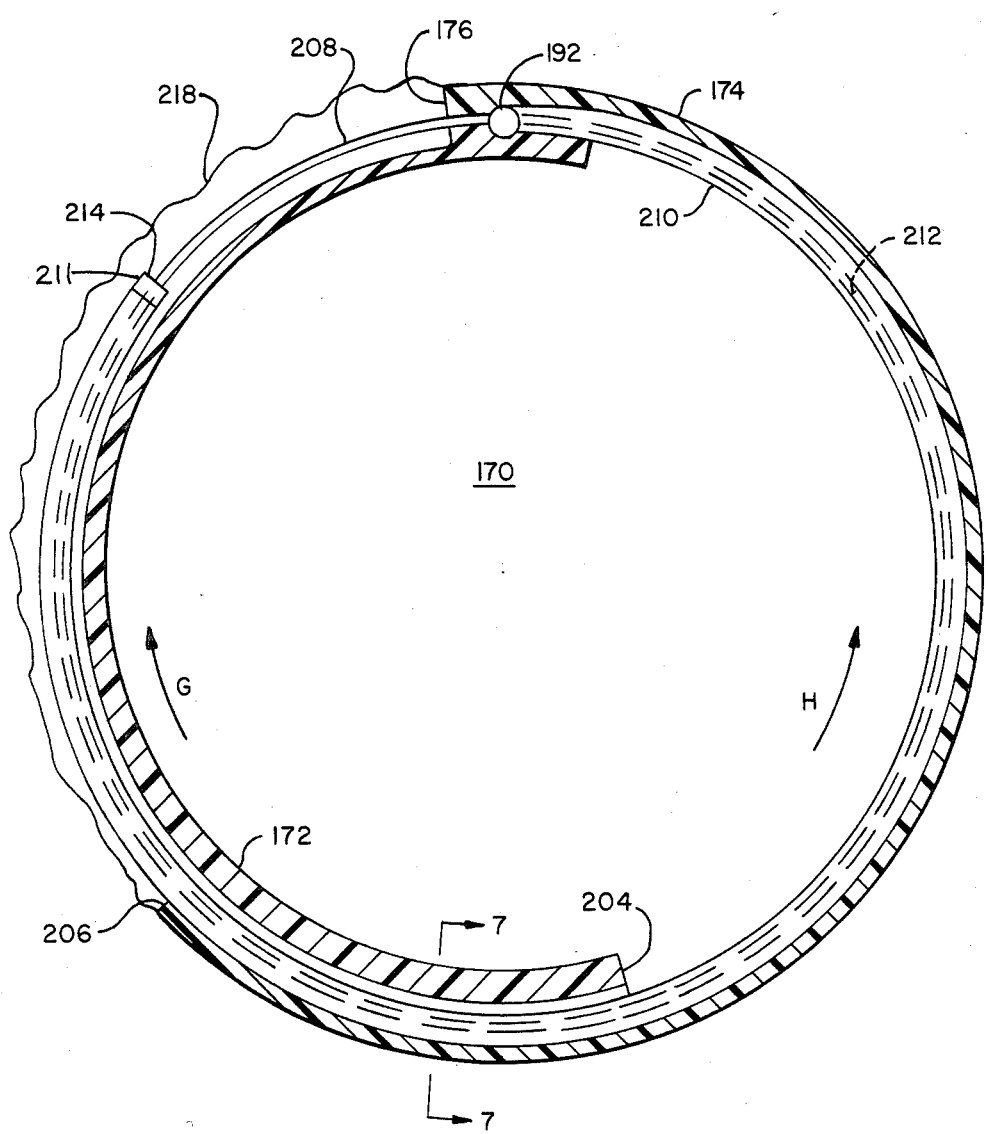
FIG. 6 is a view along 6—6 of FIG. 5.

In another preferred embodiment of this invention, referring to FIGS. 5 and 6, there is shown an endotracheal tube 170 of similar material in which the transversely curved segments 172 and 174 are fused together through an extended coupling 176 along one overlapping edge of each segment.

Indicated schematically in FIG. 5 are the locations of identical expansion joints 178, 182, and 184, and a pair of identical slidable dovetail joints 186 and 188. A supply line consisting of passageway 192, which is indicated schematically in FIG. 5, is located within coupling 176 as shown in FIG. 6. Access to passageway 192 is through an opening 194 into which a tube 196 is inserted for the delivery of air under pressure from an adaptor 198 and a bellows 202 as described in connection with the embodiment illustrated in FIGS. 1-4.

As shown more clearly in FIG. 6, segments 172 and 174 terminate at 204 and 206, respectively, thereby overlapping for a distance. Extending out of passageway 192 are a pair of hollow catheters 208 and 210 extending circumferentially around tube 170 between segments 172 and 174. The outside diameter of catherter 208 is less than the inside diameter of catheter 210 so that the former slides inside the latter as illustrated. Catheter 208 terminates within catheter 210 at 212, while catheter 210 terminates at 214. Catheter 210 may be fused to the inside wall of outer segment 174. Diaphragm 218 may be employed to enclose exposed edges of segments 172 and 174. A rubber membranous injection site 211 may be formed at the opening into catheter 210 to prevent air leakage.

In the operation of endotracheal tube 170, once it has been inserted into a patient, passageway 192 would be pressurized using a syringe connected to adaptor 198 as previously described. As catheters 208 and 210 become pressurized, catheter 208 would be driven out of catheter 210 thereby causing segment 172 to move in the direction of arrow G, and segment 174 to move in the direction of arrow H. Diaphragm 218 will stretch and it will limit the size of the expansion if the expansion does not otherwise come to a halt. Diaphragm 218 will also prevent leaking of air out of tube 170.

In the arrangements which have been described, it is seen that it is possible to insert an endotracheal tube incorporating the principles of this invention through very narrow openings without sacrificing passageway space so that there is less of a penalty when it has to be inserted through the nasal cavity. In addition, the tube can be especially useful for use with children where a much narrower tube must be employed and the use of a cuff is contra indicated. The designs are simple and economical permitting the apparatus to be made disposable while at the same time being highly reliably and extremely safe to use.

While only certain preferred embodiments of this invention have been described, it is understood that many variations of this invention are possible without departing from the principles of this invention.

For example, in FIGS. 1-4, instead of a catheter tube, outer segment at the expansion joints could be provided with a hollow protruberance in which there is a passageway for the pressurizing gas and the stilet. Supply line 34 might be placed on the inside or outside of the male oriented segment 12 or 14, and under certain conditions there may be employed two stilets with pressurized gas being supplied outwardly rather than inwardly in the embodiment described.

With pediatric tubes, or tubes less than 6 mm. ID, in the distal portion of the tube, specifically the glottic and subglottic portion, the two segments can be joined together only by a plurality of spaced slidable dovetail joints omitting the slidable expansion joints. The reason for this is because of the reduced wall size of endotracheal tubes of small diameter. Since the distance or length of the tube from the glottic to the distal end of the tube is short, the most distal slidable expansion joint could easily control the expansion of the distal segment. Above the glottis, for example, the proximal $\frac{2}{3}$ of the tube could consist of a slightly thicker wall to easily accommodate the slidable expansion joints and yet maintain a constant uniform internal diameter of said tube.

It is therefore understood that various changes and omissions are possible without departing from the principles of this invention as indicated by the scope of the claims which follow.

What is claimed is:

1. An endotracheal tube and the like comprising:
   a. an extended tube-like member having expansion joint means at spaced locations for permitting circumferential expansion of said member at each location to an extent permitted by the space in the trachea surrounding said member at each location;
   b. means to deliver gas under pressure to said tube-like member;
   c. said joint means including means to permit said circumferential expansion; and
   d. means responsive to gas pressure for effecting the actuation of said joint means causing said circumferential expansion at each said location.

2. The endotracheal tube of claim 1 in which said tube comprises a pair of segments fused together in a section along one lengthwise edge the length of said tube overlapping circumferentially, said joint means causing during expansion the relative movement of said segments circumferentially to increase the size of the tube at each location.

3. The endotracheal tube of claim 1 having slidable dovetail joint means between said overlapping segments to prevent relative axial movement of said segments.

4. The endotracheal tube of claim 3 having passageway means in said fused section for conveying gas under pressure, a pair of oppositely directed hollow catheter means extending out from said passageway means at each joint means, one of said catheter means entering the other of said catheter means, the outer edge of said catheter means being fused to one of said segments, whereby pressurization within said passageway will cause expansion circumferentially of said tube.

5. The endotracheal tube of claim 4 having means to prevent leakage of pressurized gas and limit the expansion of said tube.

6. A device for insertion into a body opening comprising:
   a. an extended tube-like member comprising a pair of first and second extended transversely curved segments, said first segment overlapping said second segment;
   b. means comprising slidable expansion joint means responsive to gas pressure between said first and second segments to permit relative sliding movement between said segments along a circumference of said tube-like member thereby permitting the circumference of said member to be altered; and
   c. gas pressurizing means for actuating said segments at said expansion joint means to cause said segments to slide with respect to each other to expand the circumference of said member at said joint.

7. The device of claim 6 having means for delivering a gas under pressure to said expansion joint means.

8. The device of claim 7 in which said expansion joint means comprises cylinder means containing piston means for receiving and acting under the pressure of said gas to expand said member.

9. The device of claim 8 in which said cylinder means comprises tubular catheter means communicating with said means for delivering gas circumferentially disposed about said tube-like member terminating at a pair of exposed edges.

10. The device of claim 9 in which said piston means comprises an extended member entering said tubular means at both of said exposed edges.

11. The device of claim 1 having slidable dovetailed joint means between said first and second segments to insure only circumferential relative motion between said segments.

12. The device of claim 7 in which said segments are fused in a section lengthwise along one overlapping edge of each segment.

13. The device of claim 12 in which said means for delivering gas comprises a passageway in the fused section.

14. The device of claim 13 in which a pair of hollow catheters extend in opposite directions and circumferentially to communicate with said passageway, one catheter being fused to the inside of the outer segment, the second catheter entering said first catheter, where pressurization of said passageway will cause expansion of said tube by sliding of the free ends of said segments in opposite directions.

15. A device for insertion into a body opening comprising:
   a. an extended tube-like member comprising a pair of first and second extended transversely curved segments, said first segment overlapping said second segment;
   b. multiple actuating means responsive to pressurized gas at locations spaced along the length of said device between first and second segments to effect relative sliding movement between said segments along a circumference of said tube-like member at each location thereby permitting the circumference of said member to be enlarged at each actuating means by an amount determined by the available room for expansion at each location; and
   c. means adjacent the proximal end of said device to deliver a gas under pressure for effecting operation of said actuating means.

16. The device of claim 15 in which the effecting means comprises means to deliver gas under pressure to said actuating means.

17. The device of claim 15 having means to prevent leakage of said gas and to limit the expansion of said tube-like member.

18. The device of claim 15 in which each said actuating means comprises a circumferentially arranged tubular means with spaced open ends in said first segment, and piston means extending over said second segment into said tubular means at both ends forming a piston and cylinder arrangement.

19. The device of claim 18 in which said actuating means delivers gas under pressure to said tube-like member, and means within said tube-like member to deliver said gas under pressure to said tubular means.

20. The device of claim 19 having dovetail joint means slidable along a circumference of said device to prevent relative motion in an axial direction of said segments.

* * * * *